United States Patent [19]

Debregeas et al.

[11] Patent Number: 4,960,596

[45] Date of Patent: Oct. 2, 1990

[54] SLOW-RELEASE PREPARATION OF DILTIAZEM, AND A MEDICINE PROVIDED THEREBY

[75] Inventors: Patrice Debregeas, Versailles; Gerard Leduc, Malesherbes; Jean-Francois Boyer, Houdan, all of France

[73] Assignee: Ethypharm, Houdan, France

[21] Appl. No.: 275,354

[22] Filed: Nov. 23, 1988

[30] Foreign Application Priority Data

Nov. 26, 1987 [FR] France ............................ 87 16425

[51] Int. Cl.⁵ .............................................. A61K 9/56
[52] U.S. Cl. .................................... 424/458; 424/459
[58] Field of Search ................................ 424/458, 459

[56] References Cited

U.S. PATENT DOCUMENTS 4,721,619 1/1988 Panoz et al. ...................... 424/468

Primary Examiner—Merrell C. Cashion, Jr.
Assistant Examiner—Leon R. Horne
Attorney, Agent, or Firm—Joseph S. Iandiorio

[57] ABSTRACT

The slow release preparation obtained by the method of the invention reduces the number of times the medicine needs to be taken per day, and also provides lower peaks of concentration in the blood after the medicine has been taken while simultaneously ensuring that the lowest concentration in the blood remains higher over a period of time.

9 Claims, 11 Drawing Sheets

SLOW-RELEASE PREPARATION OF DILTIAZEM, AND A MEDICINE PROVIDED THEREBY

The present invention relates to a new Galenical preparation of Diltiazem hydrochloride (referred to below as Diltiazem for short) and its method of preparation.

BACKGROUND OF THE INVENTION

This substance has the following formula:

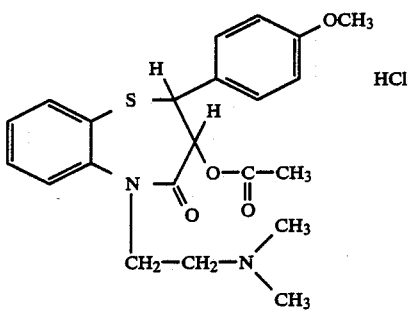

It comes in the form of a powder or white crystals, is odorless, and has a melting point lying between 208° C. and 212° C. Diltiazem is known to inhibit the inflow of calcium through the special channels to be found in the membranes of a variety of cells. By this mechanism, it exerts a depressive effective on heart pacemaker activity and on auriculo-ventricular node conduction resulting in a negative chronotropic effect. Diltiazem appears to have a weak negative inotropic effect on the heart muscle and it gives rise to vasodilatation of smooth muscle. Diltiazem reduces intra-cellular sodium by stimulating the sodium-potassium pump of smooth muscle cells and of other types of cell. This effect is responsible for membrane stabilizing effects and for its diuretic (non-vascular) action on renal tubules. Clinically, Diltiazem is used above all as an anti-angina remedy, both against chronic stable angina and against unstable angina. It also has activity against arythmia and may be used in other cardiovascular complaints such as congestive cardiac insufficiency and Raynaud's syndrome, and also in peripheral and cerebral circulatory insufficiency.

Diltiazem is also under close study for hypertension, and is already an indication recognized by the authorities in many countries.

It is a substance which has few side effects, in particular when compared with other calcium antagonistic substances such as Nifedipine or Verapamil, and it can thus be considered for use in long-term treatment.

At present, Diltiazem is used in the form of immediate-release pills having doses of 30 mg, 60 mg, and 90 mg. Recommended dosage is 180 mg taken two or three times a day, up to 240 mg or even 360 mg in severe cases.

The literature shows that Diltiazem is absorbed very rapidly and that its concentration peak is reached between three and a quarter hours and four hours. Its half life is four hours to seven hours. The phenonemom of saturation to therapeutic doses is not observed, and consequently the medicine does not accumulate after repeated administration. Tolerance to Diltiazem is very good. Considerable variability has been observed in the pharmacokinetic parameters of different subjects, which makes it difficult to maintain plasma concentration in the therapeutic window. This information, together with experience acquired while developing numerous products, has led the Applicant to attempt to optimize the currently existing Galenical preparation of Diltiazem by selecting a sustained- or slow-release preparation in the form of capsules, pills, or sachets containing microgranules.

The slow-release preparation should reduce the number of times the medicine is taken per day by extending the time over which the substance is released so as to enable the medicine to be taken, if possible once a day, or at most twice a day. Thus, in order to improve patient comfort, by avoiding too many occasions in the day when the medicine needs to be taken (with the attendent risk of wrong dosage), and also to reduce the risk of undesirable effects related to very high concentration peaks in the blood, the present invention seeks to maintain the blood concentration in an equilibrium state having a minimum of 40 ng/l and a maximum that does not exceed 300 ng/ml. This result cannot be obtained by taking the usual preparations or types of immediate action pill or delayed action pill as commercially available in Europe only once or twice a day, since the available pills and preparations do not make it possible to remain within the above-specified blood concentration limits. In addition, the selected microgranular form of preparation improves dispersion of the active substance. After the capsule opens, the microgranules spread widely through the digestive tract and increase the contact area between the active substance and digestive liquids, thereby ensuring good distribution of the medicinal effect by improving absorption. Further, by splitting up the unit dose into minute fractions, it is impossible for a high concentration of active substance to build up at a given point in the digestive tract, and this serves to reduce local intolerance and also to reduce intra- and inter-patient variations.

Prior art attempts have been made to prepare Diltiazem in the form of microgranules. Thus, European patent application number 0 149 920 filed in the Name of Elan Corporation plc describes microgranules containing Diltiazem in association with an organic acid and a lubricant inside an outer membrane (as defined by United States Phamacopea No. 21, or USP No. 21 for short) which does not make it possible to obtain satisfactory concentrations in the blood flow (i.e. not less than 40 ng/ml) without the appearance of unwanted side effects when taken only once or twice a day for daily doses lying in the range 100 mg to 500 mg, and preferably in the range 150 mg to 400 mg. Further, the stability of such microgranules can be affected by the presence of organic acids which may have an influence on the physiochemical characteristics of the outer or inner membranes coating the microgranules.

SUMMARY OF THE INVENTION

The Galenical preparation of the invention is remarkable in the sense that it is constituted by microgranules containing Diltiazem in the center and an outer membrane enabling prolonged release of Diltiazem into an aqueous medium with said release, measured in accordance with United States Pharmacopea No. 21, lying within the following limits:

(a) between 5% and 35% after one hour;
(b) between 15% and 40% after two hours;
(c) between 20% and 50% after three hours;
(d) between 30% and 75% after four hours;

(e) between 40% and 80% after six hours; and
(f) between 55% and 95% after eight hours.

The core has a diameter of 0.2 mm to 0.5 mm and is constituted by neutral excipients, e.g. about 75% saccharose or fructose and 25% starch.

In a variant of the method of the invention, neutral microgranules are inserted in a pill-coating turbine, with the microgranule size lying preferably between 0.2 mm and 2 mm.

A solution of polyvinylpyrrolidone (PVP) is prepared in water or a solubilizing organic solvent (e.g. ethylalcohol, or acetone), and the microgranules are wetted with the PVP solution and a quantity of the active substance is projected until the granules are dried. The operation is repeated until the quantity of active substance corresponding to the desired dose has been used up.

Thereafter, the microgranules are dried in hot air and/or by passing them through a desiccation enclosure. They are then sieved and checked for humidity and grain size.

Numerous types of coating may be used to make an outer membrane in accordance with the invention. According to the invention, such coatings should be considered as being equivalent providing they make it possible to obtain products which are biologically equivalent to those described below by way of non-limiting example, with bio-availability results being given below for products corresponding to said examples in order to make it possible for the person skilled in the art to appraise said biological equivalence.

BRIEF DESCRIPTION OF THE DRAWINGS

Implementations of the invention are described by way of example with reference to the accompanying drawings, in which.

MORE DETAILED DESCRIPTION

In a first series of examples, the main component of the outer membrane of the Galenical preparation is a mixture of shellac and ethylcellulose.

In this case, a solution of shellac and ethylcellulose in alcohol is prepared for coating purposes together with an appropriate quantity of talc. The alcohol solution of de-waxed shellac and ethylcellulose is applied while simultaneously projecting talc. Drying is performed in hot air, after which the grains are sieved, and humidity and grain size are checked.

After the product has been accepted, by passing the checks performed during manufacture, the microgranules are put into capsules, or pills are made containing the microgranules.

The characteristics of the outer membranes of the microgranules obtained in this way should enable Diltiazem to be released into an aqueous medium over the following intervals as measured using the method of USP No. 21:
10% to 20% after one hour;
30% to 45% after four hours; and
60% to 75% after eight hours.

To do this, a solution of de-waxes shellac and ethylcellulose in alcohol was used having the following dry weight proportions: 70 parts shellac per 30 parts ethylcellulose, by weight.

Different preparations of microgranules having an outer coat containing shellac have the following ingredients as listed in Table I lying within the weight ranges expressed as a percentage of the total weight of the finished product (bulk microgranules).

TABLE I

| INGREDIENTS | WEIGHT RANGE (%) |
|---|---|
| Neutral granule | 8 to 15 |
| Diltiazem | 60 to 85 |
| Polyvinylpyrrolidone | 4 to 6 |
| Shellac | 2 to 5 |
| Ethylcellulose | 1 to 3 |
| Talc | 0 to 10 |

Figure 1:
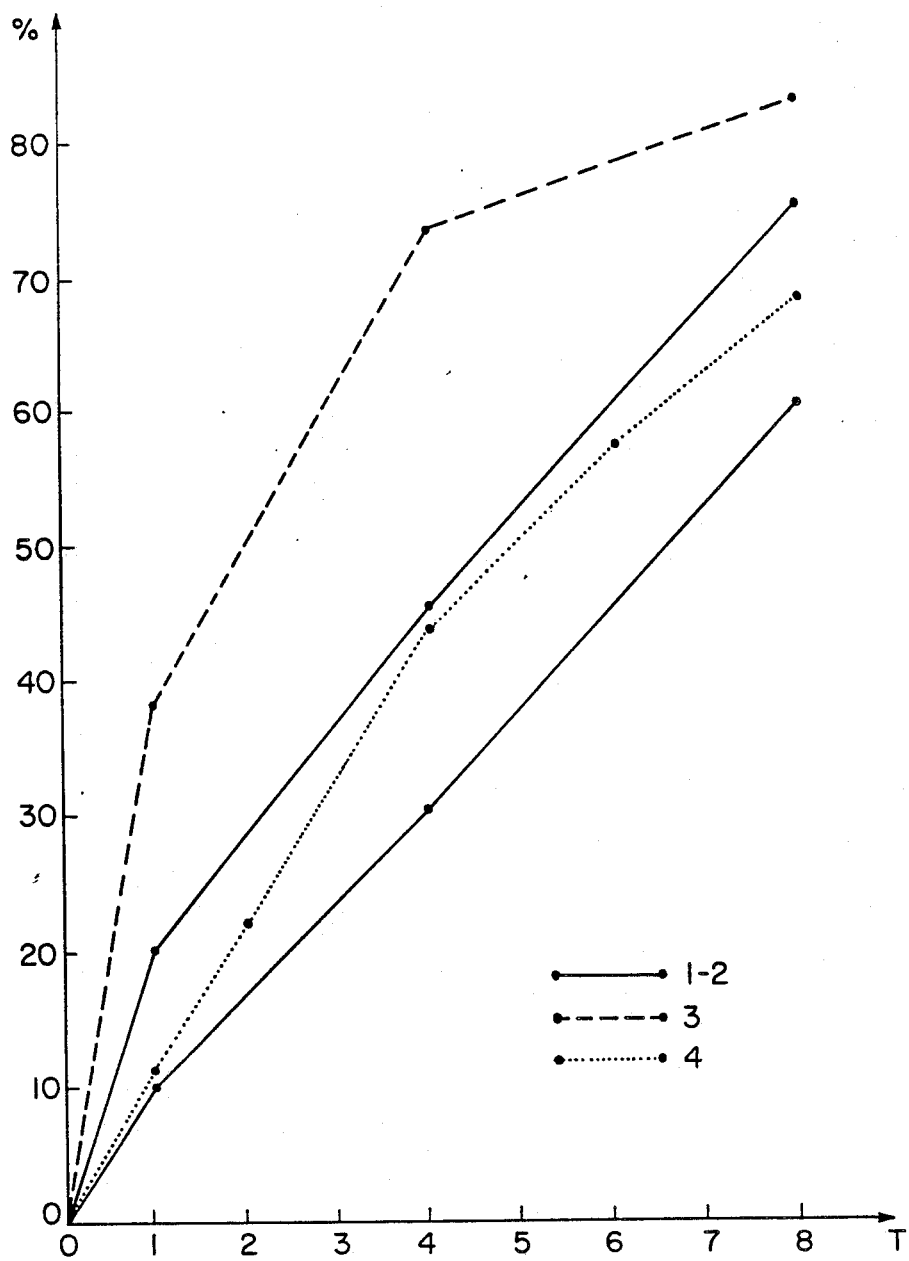
FIGS. 1 and 2 are graphs applicable to first and second implementations of the invention respectively showing accumulated percentage active substance released as a function of time in hours.

FIG. 1 is a graph showing the in vitro release curves of preparations having an outer layer including shellac and obtained using the method of USP No. 21. Curves No. 1 and 2 give the limit values corresponding to the preferred intervals as specified above, Curve No. 3 corresponds to a preparation having 3.50% by dry weight of shellac and ethylcellulose, and 9.5% talc, which preparation does not meet the standards of the invention, and curve No. 4 corresponds to a preparation having 4.75% by weight of shellac and ethylcellulose, and 9.90% by weight of talc, which preparation does meet the standards of the invention.

Bioavailability results obtained using the preparation of curve No. 4 in FIG. 1 are also shown. These results are given in accompanying Table II for three different dosages per dose (180 mg, 240 mg, and 300 mg of Diltiazem per capsule) which are the three dosages considered as being advantageous after trials performed by the Applicant concerning effective periods between taking doses. These bioavailability studies shown in Table II were performed on 24 volunteers in a double blind trial using repeated doses and comparing the product of the invention (SR) with a product commercially available under the trademark TILDIEM and sold by SYN-THELABO (pills containing 60 mg of Diltiazem). Apart from days 1 and 7 of the trials, the patients received the equivalent of 180 mg to 240 mg per day for the trials testing those dosages. For the trials testing 300 mg of SR, the dosage of the control immediate preparation was 360 mg per day. See Table II. The legend for table II appears in table IV below.

TABLE II

| Substance | Protocol | Observed Cmax in ng/ml | Observed Tmax in hours | T ½ in in hours | Accumulated AUC in ng.h/ml | Extrapolated AUC in ng.h/ml |
|---|---|---|---|---|---|---|
| 180 mg SR | Day 1 taken once a day | 99.4 | 5.7 | 7.45 | 1987.5 | 1537.2 |
| | Day 7 (equilibrium) taken once a day | 125.5 | 4.7 | 7.3 | 1695.0 | 1746.3 |
| 60 mg control | Day 1 taken 3 times | 61.5 | 16.5 | 31.1 | 977.5 | 2177.8 |

TABLE II-continued

| Substance | Protocol | Observed Cmax in ng/ml | Observed Tmax in hours | T ½ in in hours | Accumulated AUC in ng.h/ml | Extrapolated AUC in ng.h/ml |
|---|---|---|---|---|---|---|
| | Day 7 (equilibrium) taken once | 100.0 | 2.3 | 6.5 | 850.7 | 886.0 |
| 240 mg SR | Day 1 taken once | 141.2 | 5.9 | 7.9 | 1811.3 | 2291.2 |
| | Day 7 (equilibrium) taken once | 178.1 | 4.95 | 6.5 | 2424.95 | 2529.8 |
| 60 mg SR control | Day 1 2 × 120 mg doses | 103.4 | 7.4 | 16.4 | 1387.7 | 1998.5 |
| | Day 7 (equilibrium) 1 dose of 120 mg. | 172.2 | 2.7 | 5.7 | 1507.5 | 1582.8 |
| 300 mg SR | Day 1 taken once | 142.4 | 7.1 | 10.0 | 1877.2 | 2507.7 |
| | Day 7 (equilibrium) taken once | 201.6 | 6.6 | 7.9 | 3090.2 | 3176.1 |
| 60 mg control | Day 1 120 mg taken once | 77.7 | 4.2 | 5.3 | 687.3 | 754.6 |
| | Day 7 (equilibrium) 120 mg taken once | 176.8 | 3.1 | 6.6 | 1843.7 | 1913.1 |

Figure 3:
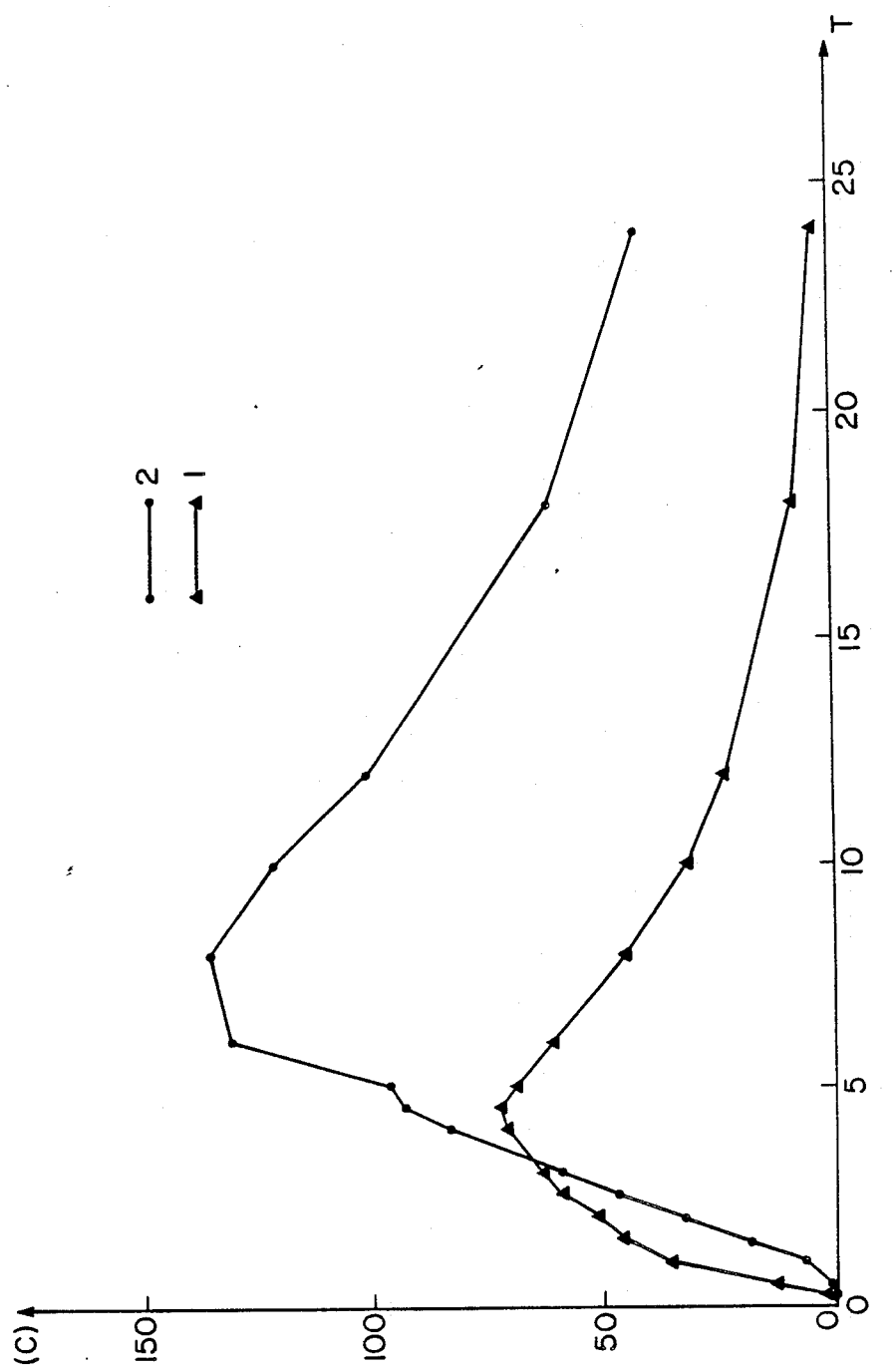
FIGS. 3 to 11 are graphs showing concentration of active substance in the bloodstream in ng/ml as a function of time in hours, for various different preparations.
Figure 4:
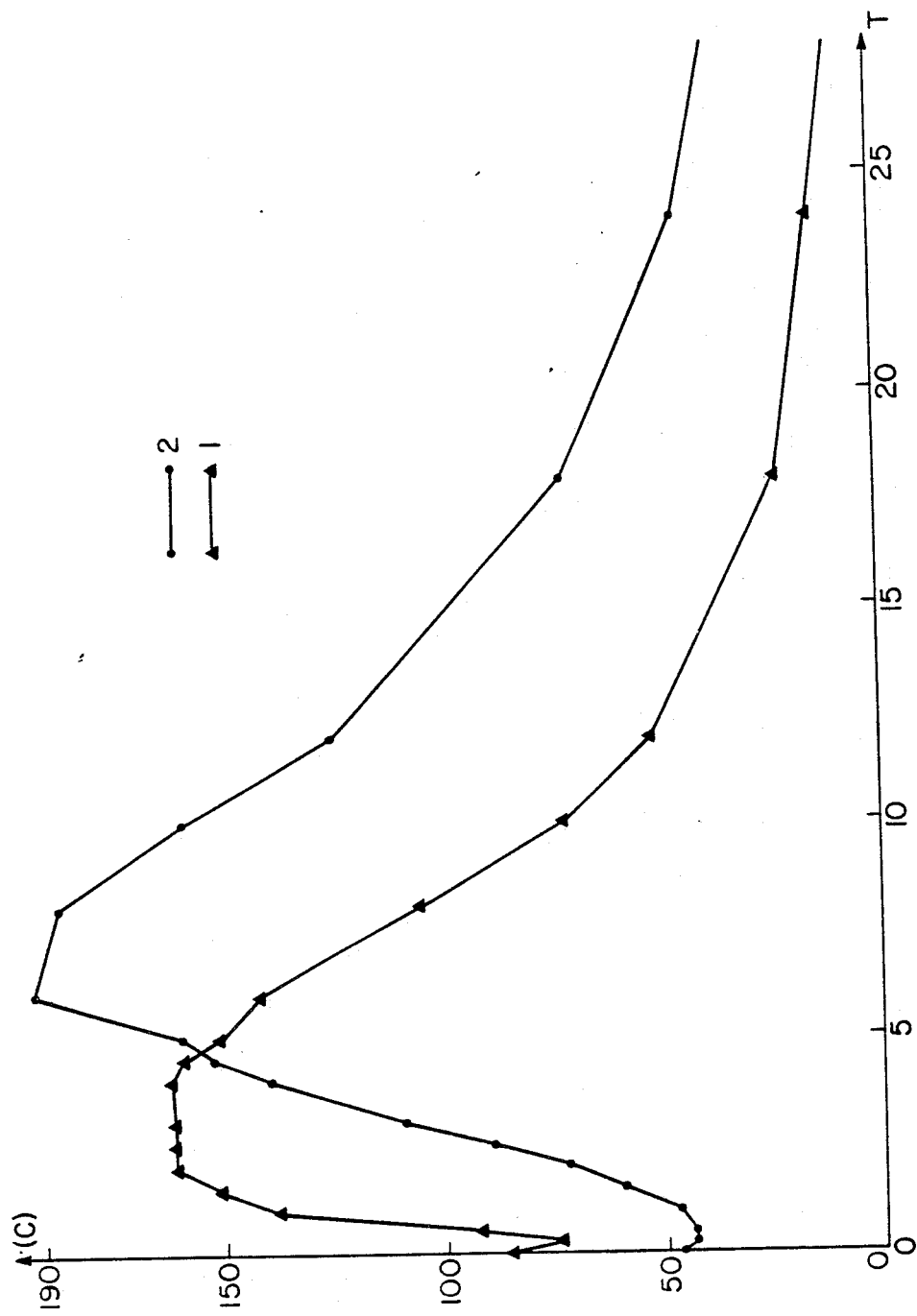
Figure 5:
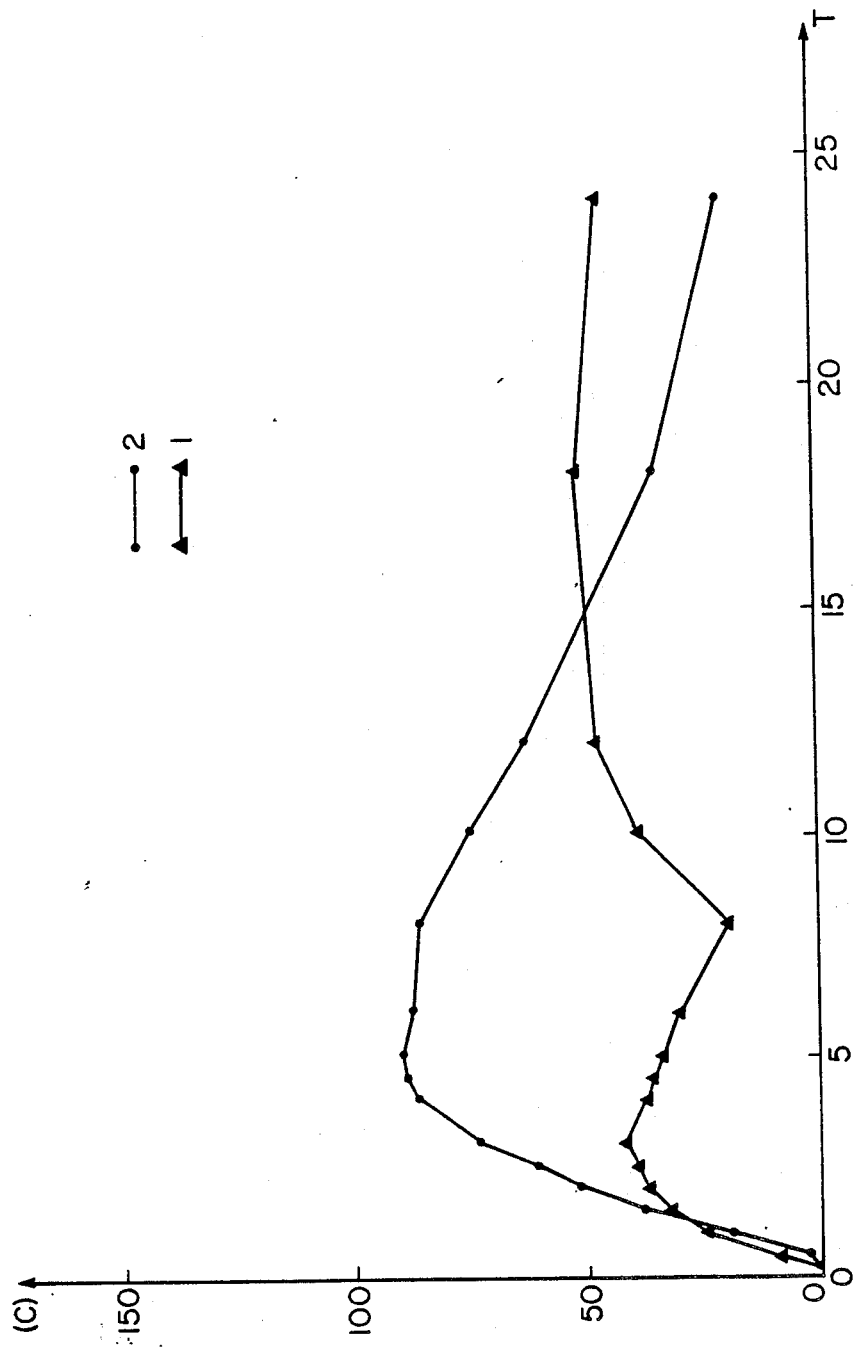
Figure 6:
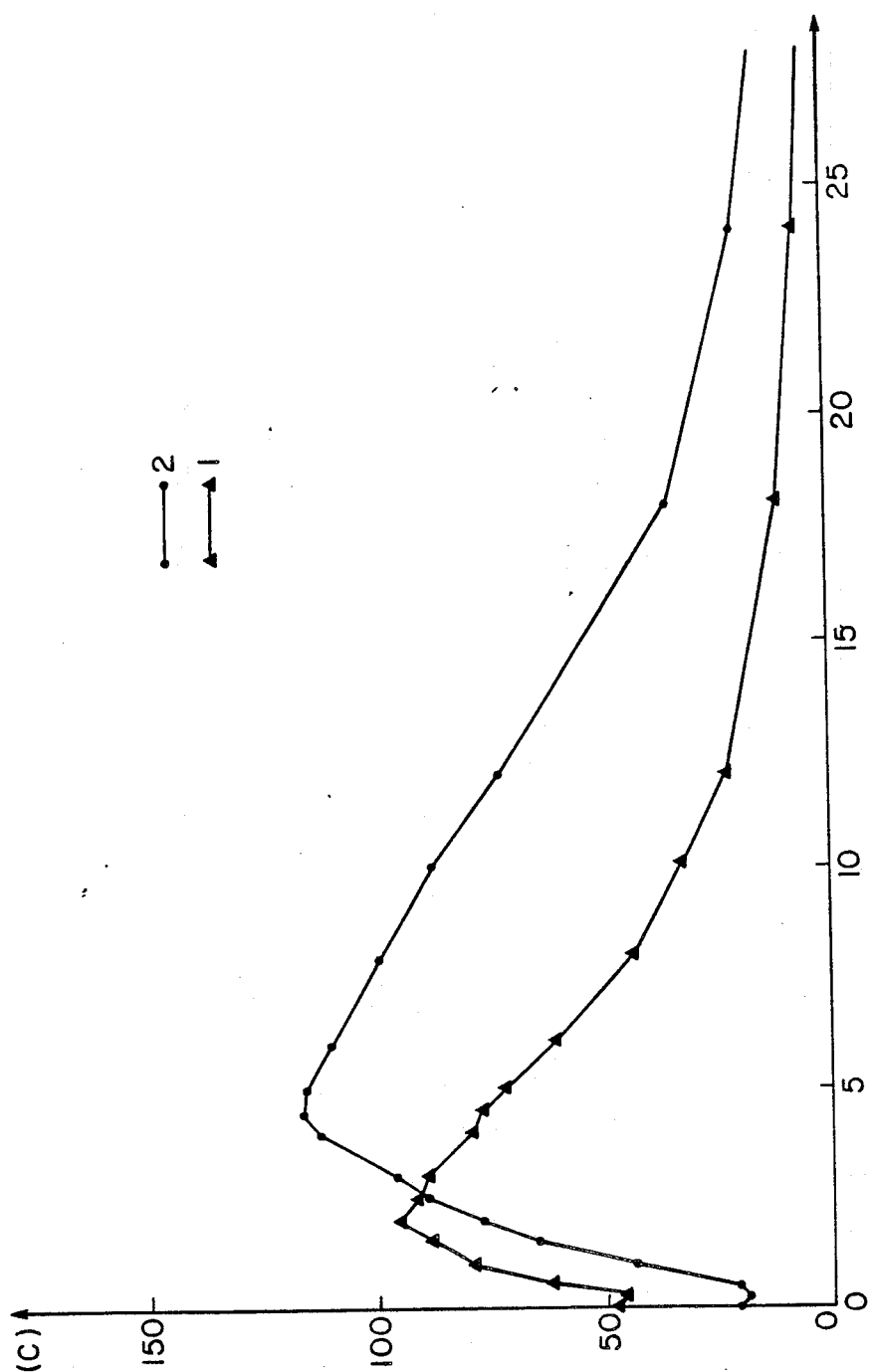
Figure 7:
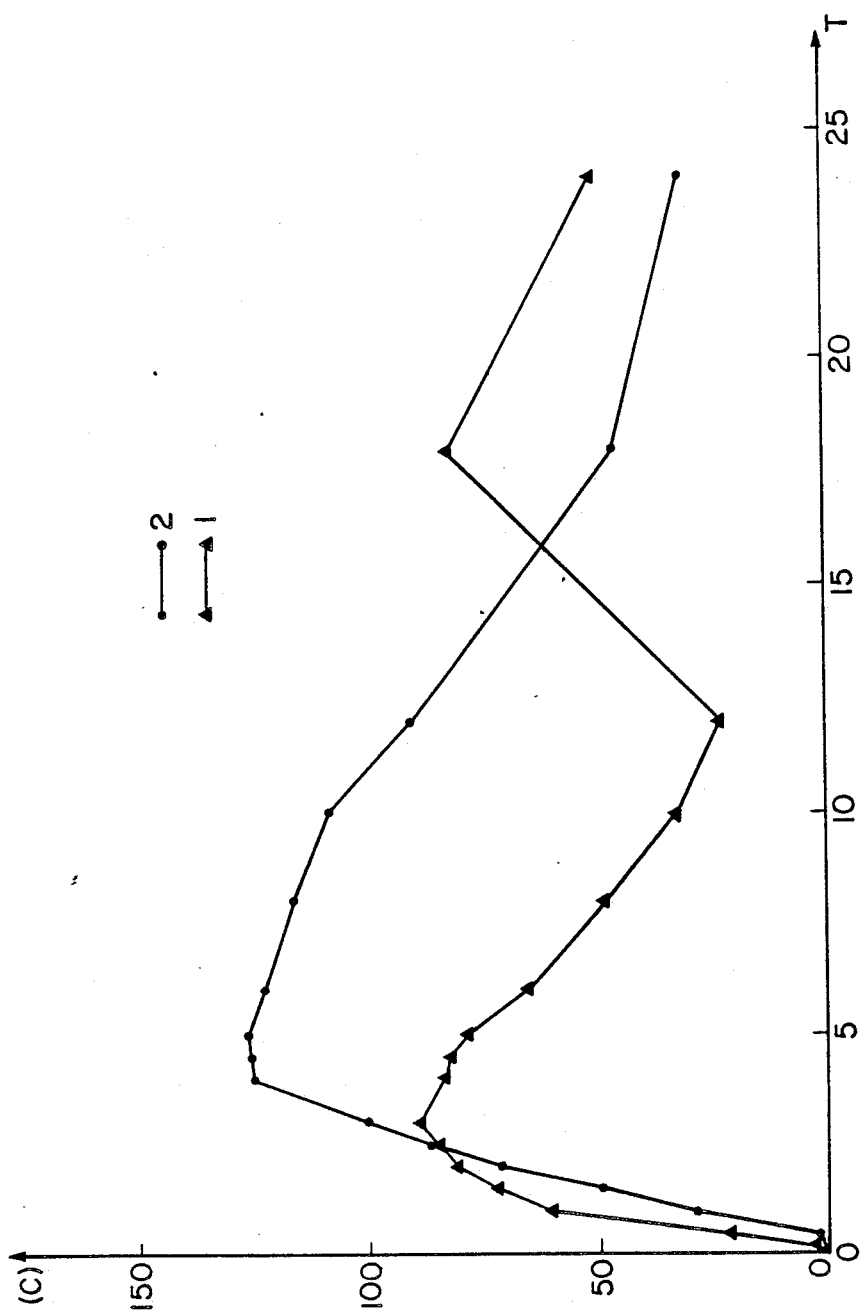
Figure 8:
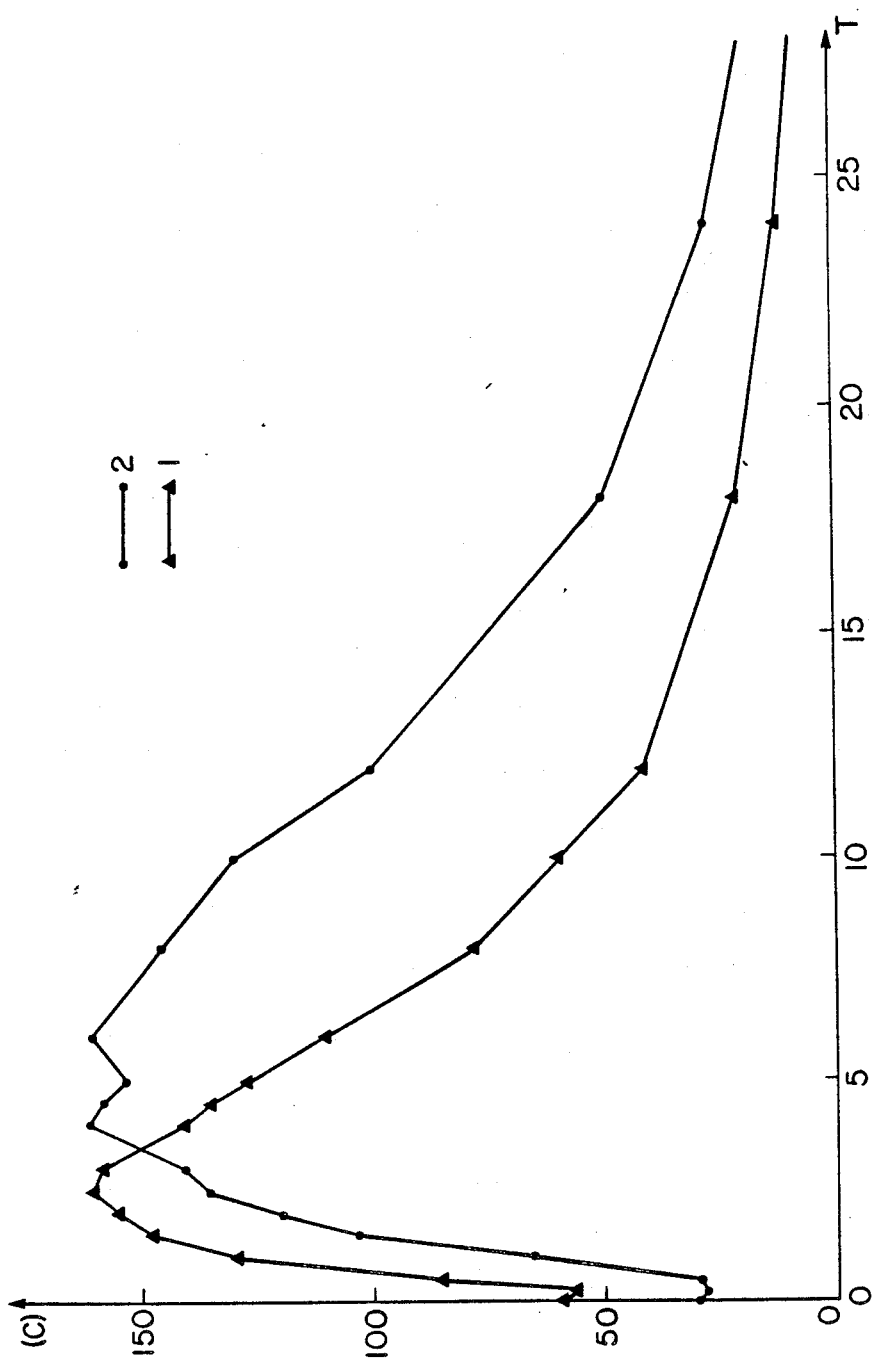

FIG. 3 shows the concentration of Diltiazem [C] in the blood expressed in nanograms per millimeter as a function of time [T] in hours for the first day (curve No. 1 for Tildiem and curve No. 2 for the product of the invention), and FIG. 4 shows the same curves for the seventh day of administering a dosage of 300 mg in accordance with the invention in comparison with three daily 120 mg doses of Tildiem over six days and one 120 mg dose taken on the seventh day. FIGS. 5 and 6 compare a dosage of 180 mg in accordance with the invention with three daily 60 mg doses of Tildiem on days 1 to 6, and one dose on day 7, respectively for the first day of the trial and for the seventh day, whereas FIGS. 7 and 8 compare a dosage of 240 mg in accordance with the invention with two daily 120 mg doses of Tildiem on days 1 to 6 and a single 120 mg dose on the seventh day.

Taken together, these results show that Galenical preparations in accordance with the invention ensure that the concentration of Diltiazem in the blood is always greater than 40 nanograms per millimeter, and consequently that they allow such preparations to be taken once only per day.

In a second series of examples, the main ingredient of the outer membrane was a mixture of Aquacoat ECD 30 and dibutylsebacate. Aquacoat is an aqueous polymer dispersion of ethylcellulose sold by the American FMC Corporation and containing 30% solids. Ethylcellulose represents 85% of these solids and the remainder is constituted by two stabilizers: lauryl sodium sulfate and cetyl alcohol.

In the following formulations, the plasticiser (e.g. the dibutylsebacate) is used at a concentration of 15% to 25% of the mass of Aquacoat expressed in terms of dry weight. The characteristics of the outer membranes of the microgranules obtained in this way should allow Diltiazem to be released into an aqueous medium over the following intervals as measured using the method of USP No. 21:

15% to 35% after one hour;
55% to 75% after four hours;
75% to 95% after eight hours.

When using an aqueous suspension of 30% ethylcellulose having dry weight proportions of 100 parts by weight together with 25 parts by weight of dibutylsebacate, the desirable limits for each ingredient used are summarized in Table III below with the ranges being expressed as a dry weight percentages compared with the total dry weight of the finished product (bulk microgranules).

TABLE III

| INGREDIENTS | WEIGHT RANGE (%) |
|---|---|
| Neutral granules | 8 to 15 |
| Diltiazem | 60 to 85 |
| Polyvinylpyrrolidone | 4 to 6 |
| Aquacoat ECD 30 | 1 to 15 |
| Dibutylsebacate | 0.4 to 4 |
| Talc | 0 to 10 |

Figure 2:
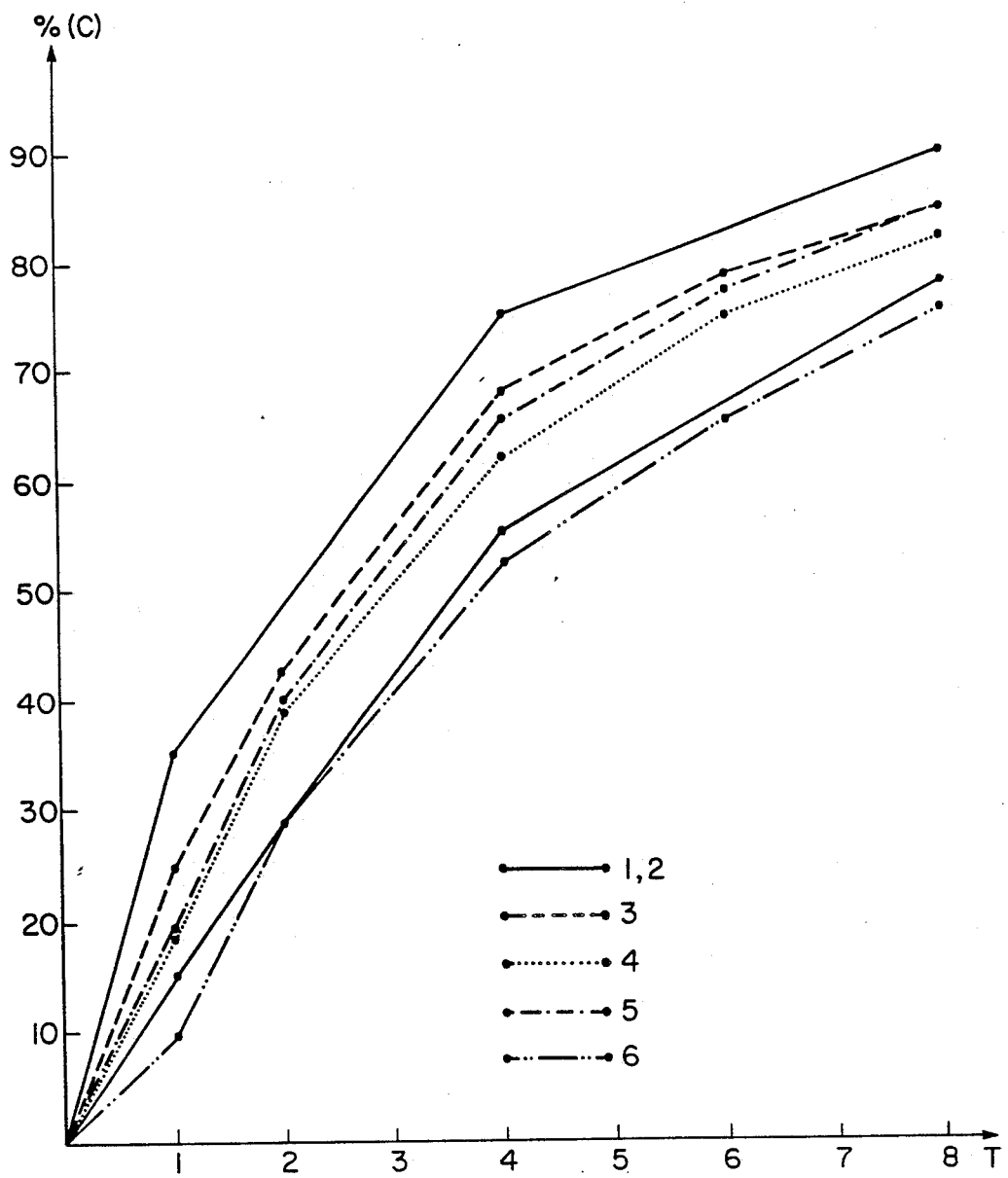

FIG. 2 is a graph similar to that used for outer layers based on shellac, but showing the in vitro release curves (using the method of USP No. 21) for the limit values corresponding to the intervals specified above (curves No. 1 and No. 2) together with three examples of talc-free formulations. The first example (curve No. 3) has 8% dry weight of the Aquacoat ECD 30 and dibutylsebacate (DBS) mixture; the second curve (No. 4) has 8.8% of ECD 30 and DBS; and the third (curve No. 5) has 9.8% ECD 30 and DBS. Each of these curves is a little slower when excipient is added. A formulation containing 15% Aquacoat and DBS is too slow (curve No. 6).

Figure 9:
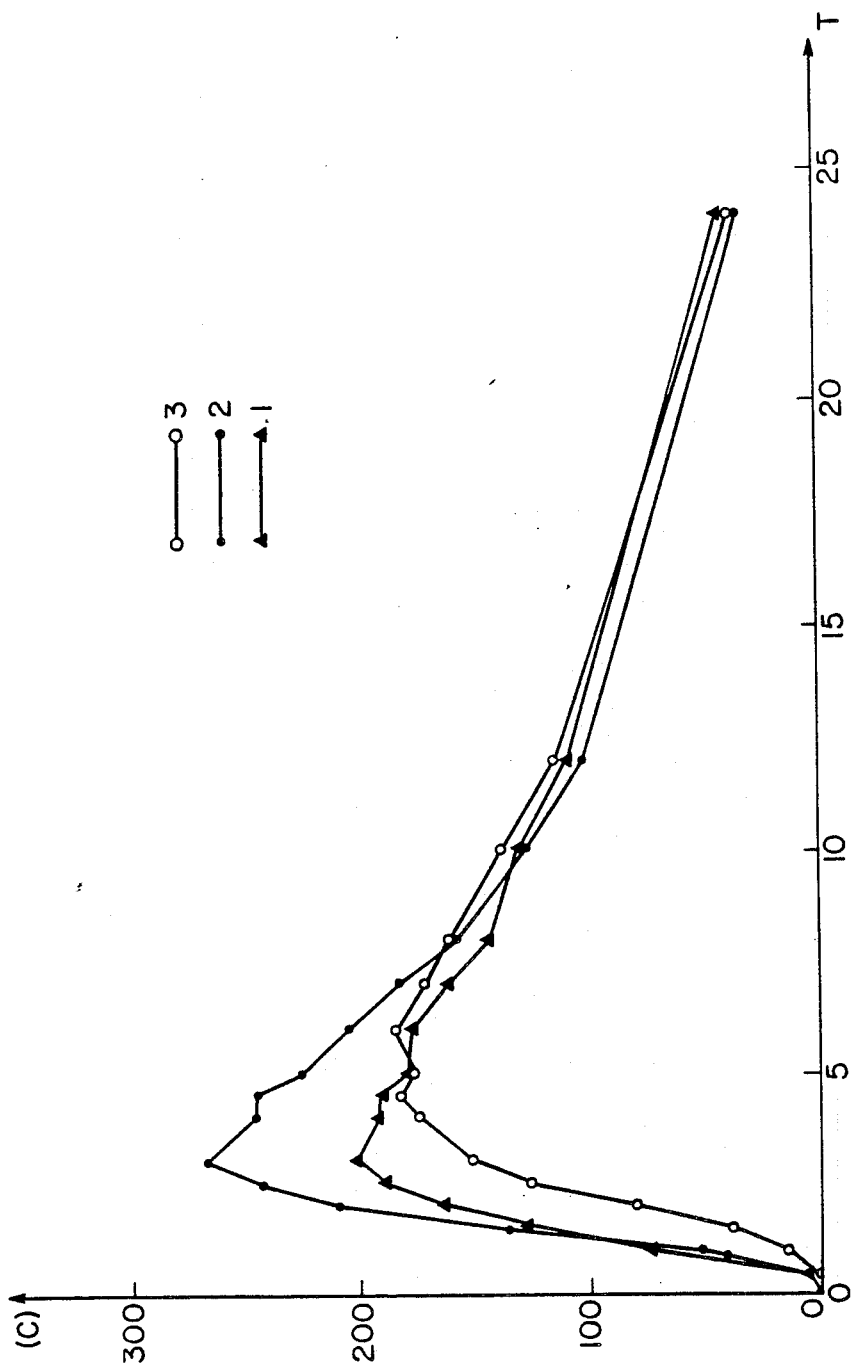

In order to show the bioequivalence of formulations including the mixture of Aquacoat and DBS in their outer membranes in comparison with formulations including the mixture of shellac and ethylcellulose, FIG. 9 shows curves giving the blood concentration of Diltiazem [C] in nanograms per milliliter as a function of time [T] in hours when administering 300 mg of Diltiazem in microgranules in accordance with the invention taken once a day by 21 volunteers, with curve 1 relating to the same formulation including shellac and ethylcellulose as curve 4 of FIG. 1, with curve 2 relating to the same formulation as curve 5 of FIG. 2, and with curve 3 relating to the same formulation of curve 3 as FIG. 2.

Figure 10:
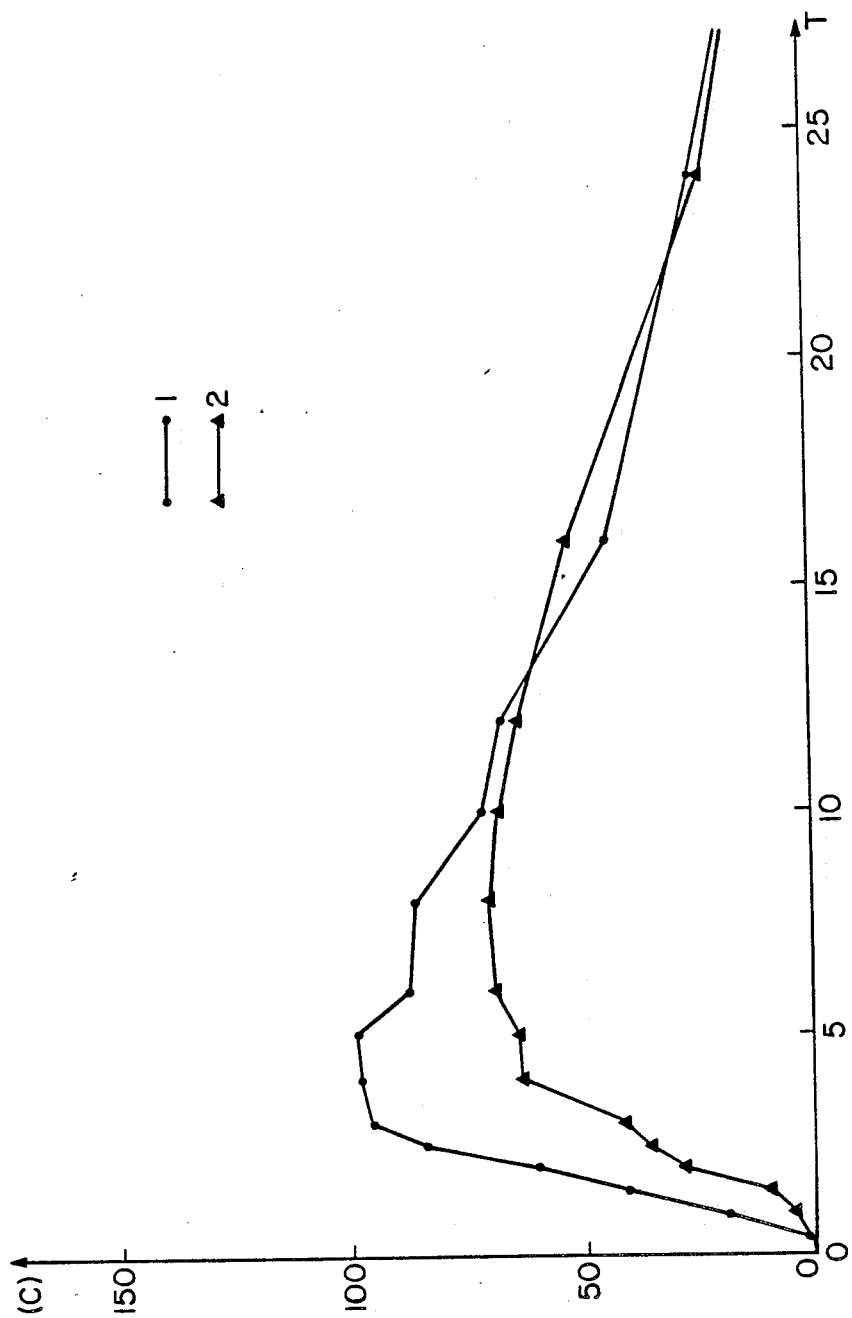

FIG. 10 shows the mean curves of trials showing the difference between a formulation including shellac (curve No. 1) corresponding to curve 4 of FIG. 1, and a formulation containing Aquacoat (curve No. 2) corresponding to curve No. 6 in FIG. 2.

Figure 11:
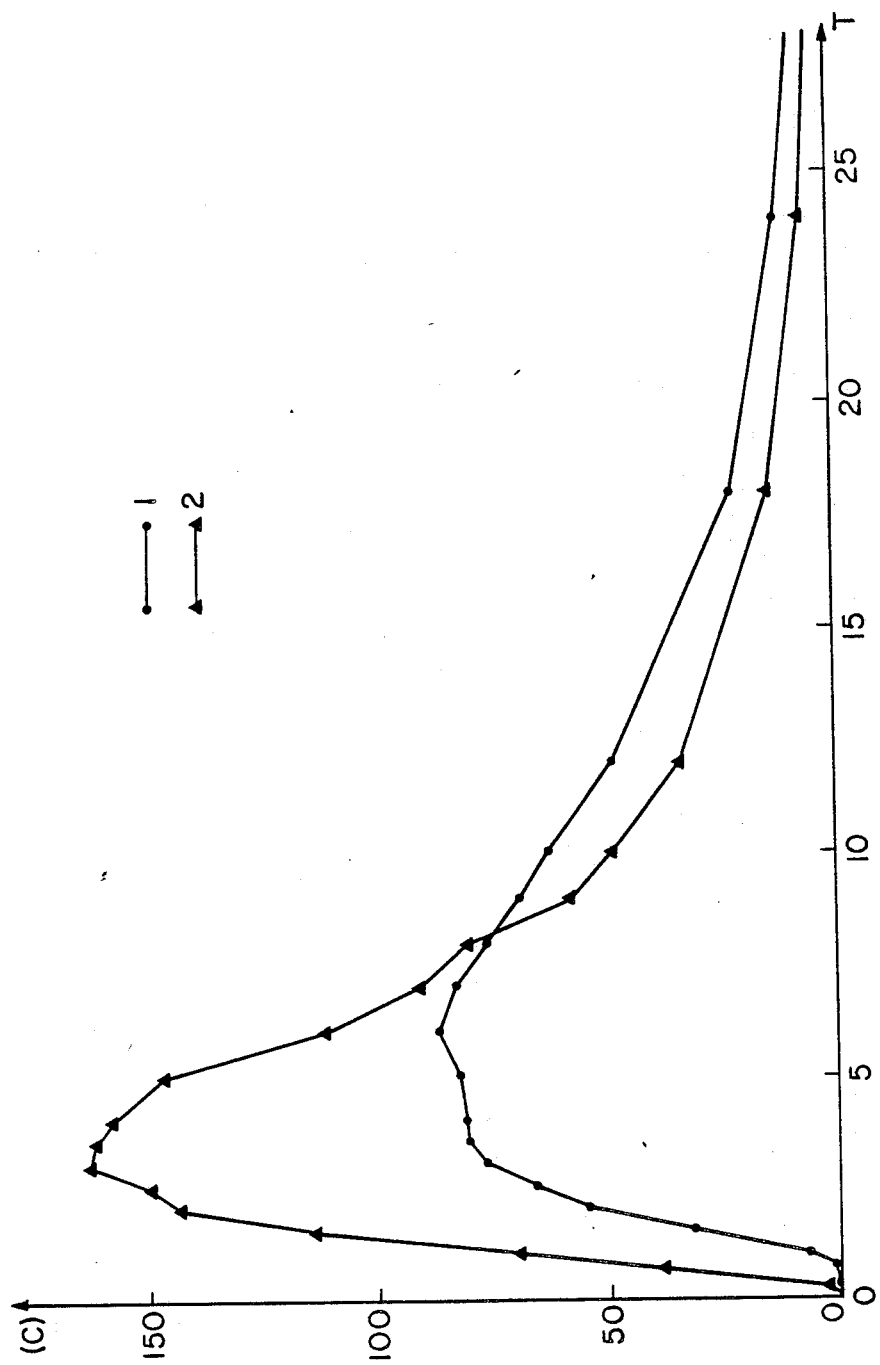

Finally, FIG. 11 shows results obtained during trials in which a single dose was taken by 18 volunteers comparing 180 mg of the formulation of table 3 (curve No. 1) with three 60 mg doses of TILDIEM (curve No. 2).

The results of these formulations are summed up in Table IV below.

TABLE IV

| | Observed Cmax in ng/ml | Observed Tmax in hours | T ½ in hours | Accumulated AUC in ng.h/ml | Extrapolated AUC in ng.h/ml |
|---|---|---|---|---|---|
| 300 mg SR shellac formulation | 218.5 | 4.2 | 8.5 | 2636.1 | 3154.3 |
| 300 mg SR aquacoat formulation (curve 3 in FIG. 9) | 375.5 | 3.0 | 7.2 | 2792.8 | 3161.1 |
| 300 mg SR aquacoat formulation (curve 2 in FIG. 9) | 201.5 | 5.6 | 7.4 | 2484.8 | 2878.7 |
| 180 mg SR aquacoat formulation | 102.15 | 5.5 | 6.4 | 1160.1 | 1193.3 |
| 180 mg control | 176.95 | 3.75 | 5.7 | 1381.9 | 1397.7 |

Legend
Observed Cmax: maximum concentration
Observed Tmax: time at which Cmax observed
T ½: elimination half life
Accumulated AUC: area under curve representing quantity of Diltiazem absorbed in 24 hours, and calculated using the trapezium method
Extrapolated AUC: area under the curve extrapolated to infinity The outer membrane of the products in Table IV has the advantage of providing formulations in which the release of Diltiazem is insensitive to pH.

Naturally, equivalent results can be obtained by using other excipients such as a suspension of ETHOCEL AQ sold by Colorcon, EUDRAGIT RL and RS or their equivalents sold by Rohm and Haas, and formulas which are equivalent according to the invention to those described above can easily be obtained by the person skilled in the art, said formulas making it possible to obtain results which are biologically equivalent to one or other of the above formulations.

All of the Galenical preparations in accordance with the invention make it possible to maintain a sufficient effective maximum concentration in the blood without any excessive concentration peak to enable the medicine to be taken once a day regardless of the indicated dosage (i.e. they maintain a concentration between 40 and 300 nanograms of Diltiazem per milliliter of blood tested). In other words, only the dosage of the single daily dose taken by the patient needs changing. Such preparations thus provide a major advantage in administering Diltiazem or pharmaceutically active salts thereof. Habitual dosages can vary between 50 mg and 500 mg per day, taken once or twice a day. If taken twice a day, it is preferable for each dose to be of 50 mg to 200 mg, and if taken once a day it is preferable to use a dose of 120 mg to 400 mg depending on whether the treatment is for angina pectoris, hypertension, or peripheral or cerebral circulation insufficiency.

No increase in toxicity of the formulations has been observed in comparison with that of Diltiazem hydrochloride in power form, and indeed there is a reduction compared with pure Diltiazem product.

Further, the stability of the formulations turns out to be excellent, in particular the stability of the formulations in the second group including Aquacoat. For formulations containing shellac, it has been observed that it is essential to eliminate all traces of sulvent at the end of manufacture. In both cases it is advantageous to heat the final mass of microgranules to about 50° C. prior to putting them into capsules regardless of whether the microgranules are prepared using the conventional turbine method or by extrusion followed by rounding and coating in a turbine or by using fluidized air bed variants, e.g. of the Glatt or Wurster type which are well known to the person skilled in the art, and which can make it possible to use the granulated active substance directly as the microgranule center element.

We claim:

1. A slow release acid-free Galenical preparation of pharmaceutically acceptable Diltiazem comprising microgranules of the type constituted by a central core coated with layers containing the active substance, with each microgranule having an outer membrane, the preparation being wherein its outer membrane is adapted to release the Diltiazem applied to the neutral core into an aqueous medium at the following rate measured using the method of the United States Pharmacopea No. 21:
   (a) between 5% and 35% after one hour;
   (b) between 15% and 40% after two hours;
   (c) between 20% and 50% after three hours;
   (d) between 30% and 75% after four hours;
   (e) between 40% and 80% after six hours;
   (f) between 55% and 95% after eight hours whereas said preparation, comprises, relative to the total weight of microgranules, 8% to 15% by weight of neutral core, layers of diltiazem comprising 60% to 85% by weight mixed with polyvinylpyrrolidone comprising 8% to 15% by weight, 0.1% to 10% by weight talc and 1% to 20% by weight outer membrane, and wherein the outer membrane comprises by weight of total microgranule weight, 2% to 5% shellac, 1% to 15% by weight ethylcellulose and 0.17to 4% by weight of plasticizer.

2. A Galenical preparation according to claim 1, wherein the outer membrane is constituted by means of an organic solution of the acetone or ethyl alcohol type containing shellac and ethylcellulose with 70 parts shellac to 30 parts ethylcellulose, said parts being parts by dry weight.

3. A Galenical preparation according to claim 2, wherein the Diltiazem is released into an aqueous medium as measured using the method of USP No. 21 at rates lying substantially between:
   10% to 20% after one hour;
   30% to 45% after four hours;
   60% to 75% after eight hours.

4. A Galenical preparation according to claim 1, wherein the outer membrane is constituted by a plasticiser of the dibutylsebacate type inserted in an aqueous suspension having 30% ethylcellulose with 100 parts by weight ethylcellulose and 15 to 25 parts by weight plasticiser with the weights being expressed in terms of dry weight.

5. A Galenical preparation according to claim 4, wherein the Diltiazem is released into an aqueous medium as measured using the method of USP No. 21 at rates lying substantially between:
   15% to 35% after one hour;
   55% to 75% after four hours;
   75% to 95% after eight hours.

6. A medicine according to claim 1, comprising the microgranules contained in a unit preparation of the capsule type at a dose of between 50 mg and 200 mg of Diltiazem per unit and intended to be taken twice a day for treating angina pectoris, hypertension, or peripheral or cerebral circulatory insufficiency.

7. A medicine according to claim 1, comprising the microgranules contained in a unit preparation of the capsule type at a dose of between 100 mg and 500 mg of Diltiazem per unit and intended to be taken once a day for treating angina poctoris, hypertension, or peripheral or cerebral circulatory insufficiency.

8. A medicine according to claim 7, including microgranules contained in a unit presentation of the capsule, sachet, or pill type, at a dose of 300 mg of Diltiazem per unit and intended to be taken once a day for treating hypertension.

9. A medicine according to claim 6 or 7, wherein the equilbrium concentrations of Diltiazem obtained in the blood flow over a day lies substantially in the range 40 to 300 nanograms per milliliter of blood sampled.

* * * * *